United States Patent
Loughran, Jr. et al.

(10) Patent No.: US 11,426,371 B2
(45) Date of Patent: Aug. 30, 2022

(54) COMPOSITIONS AND METHODS FOR TREATING CANCER

(71) Applicants: University of Virginia Patent Foundation, Charlottesville, VA (US); UNIVERSITAT DE BARCELONA, Barcelona (ES); Consejo Superior de Investigaciones Cientificas (CSIC), Madrid (ES)

(72) Inventors: Thomas P. Loughran, Jr., Charlottesville, VA (US); Gemma Fabrias, Barcelona (ES); Jose Luis Abad, Barcelona (ES); Josefina Casas, Barcelona (ES); David J. Feith, Palmyra, VA (US); Su-Fern Tan, Charlottesville, VA (US); Jennifer M. Pearson, Charlottesville, VA (US); Antonio Delgado Cirilo, Barcelona (ES)

(73) Assignees: University of Virginia Patent Foundation, Charlottesville, VA (US); Universität de Barcelona, Barcelona (ES); Consejo Superior de Investigaciones Cientificas (CSIC), Madrid (ES)

( * ) Notice: Subject to any disclaimer, the term of this patent is extended or adjusted under 35 U.S.C. 154(b) by 4 days.

(21) Appl. No.: 16/609,124

(22) PCT Filed: Apr. 27, 2018

(86) PCT No.: PCT/US2018/029747
§ 371 (c)(1),
(2) Date: Oct. 28, 2019

(87) PCT Pub. No.: WO2018/200931
PCT Pub. Date: Nov. 1, 2018

(65) Prior Publication Data
US 2020/0276138 A1    Sep. 3, 2020

Related U.S. Application Data

(60) Provisional application No. 62/491,314, filed on Apr. 28, 2017.

(51) Int. Cl.
*A61K 31/164* (2006.01)
*A61P 35/02* (2006.01)

(52) U.S. Cl.
CPC ........... *A61K 31/164* (2013.01); *A61P 35/02* (2018.01)

(58) Field of Classification Search
CPC .............................. A61K 31/164; A61P 35/02
USPC ........................................................ 514/563
See application file for complete search history.

(56) References Cited

U.S. PATENT DOCUMENTS

| 5,519,007 A | 5/1996 | Della Valle et al. |
| 2011/0071099 A1 | 3/2011 | Bielawska et al. |
| 2011/0251197 A1 | 10/2011 | Bielawska et al. |

FOREIGN PATENT DOCUMENTS

| WO | WO 2013/004871 | * | 1/2013 |
| WO | WO 2021/092543 A1 | | 5/2021 |

OTHER PUBLICATIONS

Translation of WO 2013/004871. Retrieved on Apr. 26, 2021.*
Written Opinion of the International Searching Authority corresponding to International application No. PCT/US 2018/029747 dated Jul. 11, 2018.
International Search Report corresponding to International application No. PCT/US 2018/029747 dated Jul. 11, 2018.
International Preliminary Report on Patentability Corresponding to International Application No. PCT/US 2018/029747 dated Oct. 29, 2019.
International Search Report and Written Opinion of the International Searching Authority corresponding to International application No. PCT/US 2020/59644 dated Mar. 18, 2021.
Chen et al., "ACER3 supports development of acute myeloid leukemia," Biomechanical and Biophysical Research Communications, vol. 478, pp. 33-38 (2016).
PubChem-CID 23189526.
Alvarez, S. E. et al., "Sphingosine-1-phosphate is a missing cofactor for the E3 ubiquitin ligase TRAF2." Nature vol. 465, pp. 1084-1088 (2010).
Bedia, C. et al., "A simple fluorogenic method for determination of acid ceramidase activity and diagnosis of Farber disease." J. Lipid Res. Vol. 51, pp. 3542-3547 (2010).
Camacho, L. et al., "Acid ceramidase as a therapeutic target in metastatic prostate cancer." J. Lipid Res. vol. 54, pp. 1207-1220 (2013).
Evangelisti, C. et al., "Therapeutic potential of targeting sphingosine kinases and sphingosine 1-phosphate in hematological malignancies." Leukemia vol. 30, pp. 2142-2151 (2016).
Gouaze-Andersson, V. et al., "Inhibition of acid ceramidase by a 2-substituted aminoethanol amide synergistically sensitizes prostate cancer cells to N-(4- hydroxyphenyl) retinamide." The Prostate vol. 71, pp. 1064-1073 (2011).
Grimwade, D. et al., "Molecular landscape of acute myeloid leukemia in younger adults and its clinical relevance." Blood vol. 127, pp. 29-41 (2016).

(Continued)

*Primary Examiner* — Yevgeny Valenrod
(74) *Attorney, Agent, or Firm* — Jenkins, Wilson, Taylor & Hunt, P.A.

(57) ABSTRACT

The present application provides novel compositions and methods for treating acute myeloid leukemia (AML). Compounds of the invention are acid ceramidase inhibitors, reduce AML cell viability, inhibit AML cell proliferation, increase cell death of AML cells, and induce apoptosis in AML cells. A primary compound of the invention is SACLAC: 2-chloro-N-((2S,3R)-1,3-dihydroxyoctadecan-2-yl)acetamide. The bromine analog of SACLAC (SABRAC: 2-bromo-N-((2S,3R)-1,3-dihydroxyoctadecan-2-yl)acetamide) is also useful for treating AML. SACLAC has much better activity than other know drugs used to treat AML.

17 Claims, 12 Drawing Sheets

(56) References Cited

OTHER PUBLICATIONS

Haimovitz-Friedman, A. et al., "Ceramide signaling in apoptosis." Br. Med. Bull. vol. 53, pp. 539-553 (1997).

Hatzimichael, E. et al., "Gene mutations and molecularly targeted therapies in acute myeloid leukemia." Am. J. Blood Res. vol. 3, pp. 29-51 (2013).

Howlader, N. et al., SEER Cancer Statistics Review, 1975-2013. Available at: https://seer.cancer.gov/archive/csr/1975_2013/.

Klepin, H. D. & Balducci, L. "Acute Myelogenous Leukemia in Older Adults." The Oncologist vol. 14, pp. 222-232 (2009).

Leone, G. et al., "Therapy related leukemias: susceptibility, prevention and treatment." Leuk. Lymphoma vol. 41, pp. 255-276 (2001).

Metzeler, K. H. et al., "Spectrum and prognostic relevance of driver gene mutations in acute myeloid leukemia." Blood vol. 128, pp. 686-698 (2016).

Newton, J. et al., "Revisiting the sphingolipid rheostat: Evolving concepts in cancer therapy." Exp. Cell Res. vol. 333, pp. 195-200 (2015).

Okuyama, N. et al., "Prognosis of acute myeloid leukemia transformed from myelodysplastic syndromes: a multicenter retrospective study." Leuk. Res. vol. 37, pp. 862-867 (2013).

Papaemmanuil, E. et al., "Genomic Classification in Acute Myeloid Leukemia." N. ngl. J. Med. vol. 375, pp. 900-901 (2016).

Ryland, L. K. et al., "Dysregulation of sphingolipid metabolism in cancer." Cancer Biol. Ther. vol. 11, pp. 138-149 (2011).

Spiegel, S. et al., "Signal transduction through lipid second messengers." Curr. Opin. Cell Biol. vol. 8, pp. 159-167 (1996).

Tan et al., "The emergence of acid ceramidase as a therapeutic target for acute myeloid leukemia." Expert Opinion on Therapeutic Targets, vol. 21, pp. 583-590 (2017).

Tan et al., "Acid ceramidase is upregulated in AML and represents a novel therapeutic target." Oncotarget vol. 7, p. 83208-83222 (2016).

TCGA Network, "Genomic and Epigenomic Landscapes of Adult De Novo Acute Myeloid Leukemia." N. Engl. J. Med. vol. 368, pp. 2059-2074 (2013).

Watters et al., "Targeting glucosylceramide synthase synergizes with $C_6$-ceramide nanoliposomes to induce apoptosis in natural killer cell leukemia," Leukemia & Lymphoma, 2013, vol. 54, No. 6, pp. 1288-1296, Abstract.

* cited by examiner

COMPOSITIONS AND METHODS FOR TREATING CANCER

CROSS REFERENCE TO RELATED APPLICATIONS

This application is a 35 U.S.C. Section 371 national phase application of PCT International Application Serial No. PCT/US2018/029747, filed Apr. 27, 2018, which is entitled to priority pursuant to 35 U.S.C. § 119(e) to U.S. provisional patent application No. 62/491,314, filed Apr. 28, 2017, the disclosure of which is incorporated herein by reference in its entirety.

STATEMENT REGARDING FEDERALLY SPONSORED RESEARCH OR DEVELOPMENT

This invention was made with government support under Grant No. CA 171983, awarded by The National Institutes of Health. The government has certain rights in the invention.

BACKGROUND

Acute myeloid leukemia (AML) is a malignancy of the blood and bone marrow characterized by uncontrolled proliferation of immature cells of the myeloid lineage. These cells, called blasts, overpopulate the blood and bone marrow and compromise production of normal blood cells. As an acute disease, AML is sudden onset and rapidly progressing. Only 27% of patients survive five years past diagnosis.[1] Prognosis is even worse for some groups, including those above the age of 65 and those whose disease has developed from myelodysplastic syndrome or prior chemotherapy.[2-4] In addition to the challenge of a quickly progressing disease, AML is also extremely heterogeneous in terms of clinical behavior and genetic alterations.[5-8] Genetic heterogeneity means that therapeutic agents to selectively target specific mutations are of limited benefit to most AML patients since the most common mutation only occurs in 30% of patients.[9] Thus, there is an urgent need to identify biochemical commonalities among patients in order to optimize treatment for widespread therapeutic benefit.

AML is extremely heterogeneous, and our understanding of disease biology, classification, and prognosis has been increased by recent molecular sub-classifications that contributed to a definitive update on AML diagnosis and management. These studies have comprehensively associated clinical, karyotype, and molecular profiling for large groups of patients and have identified new classification subgroups. Molecular profiling enables correlation of specific mutations or combinations of mutations with biochemical features, such as sphingolipid metabolism. Patient classification based on mutation profile has been shown to be a powerful prognostic indicator with the capability to identify subgroups that will benefit from more intensive therapeutic regimens. Others have identified prognostic relevance of DNA methylation and gene expression profiles in AML.

Sphingolipids are essential for formation of the plasma membrane and to maintain structural integrity of the cell. However, sphingolipid metabolism also produces bioactive signaling molecules that regulate cell survival and differentiation. Ceramide, sphingosine, and sphingosine 1-phosphate (S1P) represent the bioactive core of the complex sphingolipid synthetic and inter-conversion pathways. Ceramide can be cleaved by a ceramidase to produce sphingosine, which is subsequently phosphorylated by sphingosine kinase (SK) to produce S1P. Ceramide accumulation induces cell death mechanisms while S1P promotes survival through receptor dependent or independent signaling pathways that play a key role in response to therapy. Ceramide and S1P also exert opposing effects on apoptotic regulators of the Bcl-2 family. We and others have shown that ceramide decreases Mcl-1 but S1P promotes Mcl-1 expression. Mcl-1 is a key survival protein and promising therapeutic target that is able to prevent apoptosis and mediate resistance to Bcl-2 targeting agents.

Acid ceramidase (AC) is one member of the gene family that cleaves ceramides to regulate this pro-death signal. Novel work by our group utilized primary patient samples, cell lines and in vivo murine models to demonstrate AC overexpression and therapeutic potential in AML.[13] We found that AML patient samples exhibit upregulated AC expression and activity relative to normal controls.[13] This upregulation explains at least one mechanism for AML cells to enhance their survival by diverting endogenous ceramide towards the production of S1P, which is enabled by the excess sphingosine produced by AC upregulation. S1P, in turn, modulates survival through various mechanisms including receptor dependent or independent signaling pathways.[14,15] Thus, AC is positioned at the fulcrum of the "sphingosine rheostat" between the ceramide and S1P arms where it can play a pivotal role in cell death versus cell survival determination.[16] In order to validate this target, our published studies[13] utilized shRNA-mediated knockdown of AC as well as pharmacological inhibition with LCL204. However, LCL204 is an early-generation AC inhibitor with poor pharmacokinetics and significant off target effects due to its induction of lysosome permeabilization, which non-specifically leads to degradation of AC protein by lysosomal cathepsins.

There is a long felt need in the art for compositions and methods for identifying useful compounds for treating AML or developing new compounds for treating AML. The present invention satisfies these needs.

SUMMARY OF THE INVENTION

The sphingolipid metabolizing enzyme acid ceramidase (AC) exhibits increased gene expression and increased enzymatic activity in acute myeloid leukemia (AML) samples relative to normal controls (Tan et al., Oncotarget 7:83208-22, 2016). The present application discloses a new and extremely potent inhibitor of AC that unexpectedly has much greater activity than other inhibitors. A key feature disclosed herein is that the effects are more pronounced in leukemic cells than normal controls. Additionally, the present application discloses that the compounds of the invention exhibit greater activity against AML cells than previously used drugs in the art. In fact, the present application discloses unexpected results supporting the clinical application of the presently disclosed novel acid ceramidase inhibitor SACLAC in AML.

It is disclosed herein that SACLAC is not only effective against every AML cell line tested in vitro (at least thirty), it is also effective against AML cells from patient samples and is effective against a human AML cell line mouse xenograft model in vivo.

SACLAC has the chemical name and structure:

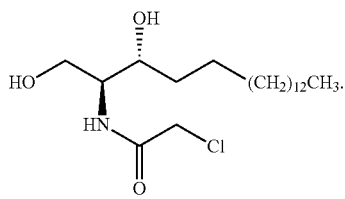

2-chloro-N-((2S,3R)-1,3-dihydroxyoctadecan-2-yl)acetamide

The present application provides compositions and methods useful for treating acute myeloid leukemia using SACLAC (2-chloro-N-((2S,3R)-1,3-dihydroxyoctadecan-2-yl)acetamide) and biologically active analogs and derivatives thereof. In addition to SACLAC, the present application discloses other compounds that can be used to treat AML.

In one aspect, the present application provides compositions and methods useful for inhibiting acid ceramidase. In one embodiment, the present invention provides acid ceramidase inhibitors that selectively target AML cells compared to otherwise identical normal hemopoietic cells.

In one aspect, treatment with SACLAC reduces S1P in AML cells.

In one aspect, treatment with SACLAC increases ceramide levels in AML cells.

In one embodiment, the compounds of the invention are useful against a cancer cell expressing higher levels of AC than its normal counterpart cells. In one aspect, the cancer is AML.

In one embodiment, a compound of the invention induces apoptosis in AML cells.

In one embodiment, a compound of the invention inhibits cell proliferation of an AML cell.

In one embodiment, treatment of a subject in need thereof with a compound of the invention significantly reduces ceramidase activity in the subject's AML cells. In one embodiment, treatment of a subject with a compound of the invention significantly reduces viability and induces apoptosis in AML cells. In one embodiment, treatment of a subject with a compound of the invention increases pro-death ceramides and decreases pro-survival S1P in AML cells. In one embodiment, treatment of a subject with a compound of the invention is more selective for AML cells than for normal cells. In one embodiment, a compound of the invention reduces leukemic burden in a subject. In one embodiment, treatment of a subject with a compound of the invention induces apoptosis in AML cells. In one embodiment, a compound of the invention regulates AC signal transduction. In one aspect, the compound is SACLAC.

The present invention further provides a pharmaceutical composition comprising a therapeutically effective amount of at least one AC inhibitor. In one aspect, the composition comprises one AC inhibitor. In one aspect, the AC inhibitor is SACLAC, or biologically active analogs or derivatives thereof. In one aspect, an additional anti-AML drug is administered to the subject (combination therapy) or another type of AML treatment is also used. In one aspect, an additional therapeutic agent is administered along with SACLAC or other compound of the invention.

In one embodiment, SABRAC, and biologically active derivatives and analogs thereof are useful for treating AML. SABRAC, which is disclosed herein to be useful against AML cells, has the following structure and chemical name:

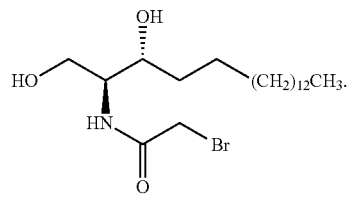

2-bromo-N-((2S,3R)-1,3-dihydroxyoctadecan-2-yl)acetamide

SABRAC is also referred to as N-[(2 S,3R)-1,3-dihydroxyoctadecan-2-yl]2-bromoacetamide.

The dosage of a compound of the invention to be administered to a subject with cancer can vary depending on such things as the type of cancer being treated and the age, sex, and health of the subject. In one embodiment, a dosage of about 0.1 mg/kg body weight to about 500 mg/kg body weight is administered. In another embodiment, a dosage of about 0.2 mg/kg body weight to about 250 mg/kg body weight is administered. In another embodiment, a dosage of about 0.3 mg/kg body weight to about 200 mg/kg body weight is administered. In another embodiment, a dosage of about 0.4 mg/kg body weight to about 100 mg/kg body weight is administered. In another embodiment, a dosage of about 0.5 mg/kg body weight to about 75 mg/kg body weight is administered. In another embodiment, a dosage of about 0.6 mg/kg body weight to about 50 mg/kg body weight is administered. In another embodiment, a dosage of about 0.7 mg/kg body weight to about 45 mg/kg body weight is administered. In another embodiment, a dosage of about 0.8 mg/kg body weight to about 40 mg/kg body weight is administered. In another embodiment, a dosage of about 0.9 mg/kg body weight to about 35 mg/kg body weight is administered. In another embodiment, a dosage of about 1.0 mg/kg body weight to about 30 mg/kg body weight is administered. In another embodiment, a dosage of about 2.0 mg/kg body weight to about 25 mg/kg body weight is administered. In another embodiment, a dosage of about 2.0 mg/kg body weight to about 20 mg/kg body weight is administered. In another embodiment, a dosage of about 3.0 mg/kg body weight to about 20 mg/kg body weight is administered. In another embodiment, a dosage of about 5.0 mg/kg body weight to about 15 mg/kg body weight is administered. In another embodiment, a dosage of about 10 mg/kg body weight to about 50 mg/kg body weight is administered. In another embodiment, a dosage of about 15 mg/kg body weight to about 45 mg/kg body weight is administered. In another embodiment, a dosage of about 20 mg/kg body weight to about 40 mg/kg body weight is administered. In one embodiment, a dosage is selected from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/kg body weight.

Administration can be made by any suitable means, including orally, intravenously, parenterally, and intraperitoneally. In one embodiment, administration can be once per day or two or more times per day. In another embodiment, administration can be once per week or two or more times per week. Compounds of the invention can also be administered as a unit dose. If necessary, a dose of the invention can be split into multiple administrations.

In one embodiment, at least two doses are administered as the treatment regimen. In another embodiment, at least five doses are administered. In yet another embodiment, at least ten doses are administered. In another embodiment, at least twenty doses are administered. In another embodiment, at least forty doses are administered.

In one embodiment, one dose is administered as a treatment regimen. In one embodiment, five or fewer doses are administered. In one embodiment, ten or fewer doses are administered. In embodiment, twenty or fewer doses are administered. In one embodiment, forty or fewer doses are administered. In one embodiment, fifty or fewer doses are administered. In one embodiment, seventy-five or fewer doses are administered. In yet another embodiment, to one hundred or fewer doses are administered. In each case, at least one dose is administered.

A treatment regimen for a subject can include, for example, multiple rounds of doses. The length of treatment can be up to six months, or five months, or four months, or three months, or two months, or one month, or up to three weeks, or two weeks. If a treatment is not successful or if it is determined that another treatment regimen is required, then a clinician can decide how to implement the next treatment regimen(s).

Doses and scheduling can be determined by one of ordinary skill in the art based on things such as the severity of the cancer and the age, sex and health of the subject.

The present application provides methods and assays for preparing or identifying new acid ceramidase inhibitors with the desired activity as disclosed herein.

A pharmaceutical composition of the invention may further comprise an additional therapeutic agent/additional therapeutically active compound.

Without wishing to be bound by any particular theory, it is hypothesized herein that SACLAC is also useful for treating other cancers overexpressing acid ceramidase.

The present application provides a kit for treating AML comprising an effective amount of a compound of the invention, an applicator, and an instructional material for the use thereof.

Various aspects and embodiments of the invention are described in further detail below.

BRIEF DESCRIPTION OF THE DRAWINGS

FIG. 1, comprising

FIG. 2, comprising

FIG. 3, comprising

FIG. 4, comprising

FIG. 5, comprising FIGS. 5A and 5B, demonstrates graphically that SACLAC induces apoptosis and reduces colony formation in primary AML cells. Multiple primary patient (Pt) AML cells were treated with various doses of SACLAC and assayed for apoptosis at 48 hours and colony formation over several days.

DETAILED DESCRIPTION

Abbreviations and Acronyms

Figure 1A:
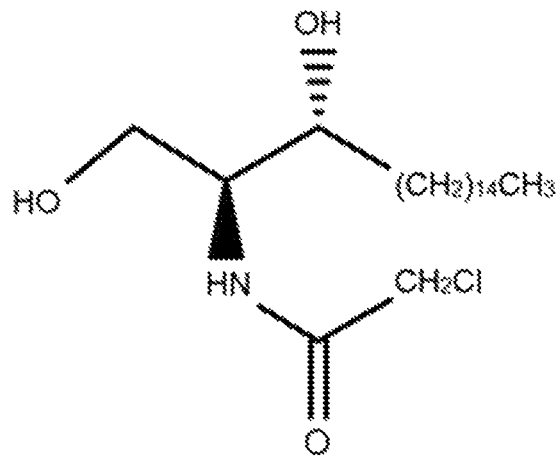
FIGS. 1A-C, shows that SACLAC treatment significantly reduces ceramidase activity in AML cell lines. Ceramide analog SACLAC (FIG. 1A) inhibits AC activity in representative human AML cell lines (FIG. 1B) HL60/VCR and (FIG. 1C) OCI-AML2 after 24 hours. Activity was assessed by incubation with a fluorogenic AC substrate. Published AC inhibitor LCL204 is included for comparison.

AC—acid ceramidase
AML—acute myeloid leukemia
h—hours or human
i.p.—intraperitoneally
i.v.—intravenously
PBMC—peripheral blood mononuclear cell
SABRAC—2-bromo-N-((2S,3R)-1,3-dihydroxyoctadecan-2-yl)acetamide SACLAC—2-chloro-N-((2S,3R)-1,3-dihydroxyoctadecan-2-yl)acetamide
S1P—sphingosine 1-phosphate
SK—sphingosine kinase Definitions In describing and claiming the invention, the following terminology will be used in accordance with the definitions set forth below. Unless defined otherwise, all technical and scientific terms used herein have the commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

The articles "a" and "an" are used herein to refer to one or to more than one (i.e., to at least one) of the grammatical object of the article. By way of example, "an element" means one element or more than one element.

The term "about", as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present invention, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the cancer being treated.

As use herein, the terms "administration of" and or "administering" a compound should be understood to mean providing a compound of the invention or a prodrug of a compound of the invention to a subject in need of treatment.

As used herein, an "agonist" is a composition of matter which, when administered to a mammal such as a human, enhances or extends a biological activity attributable to the level or presence of a target compound or molecule of interest in the subject.

As used herein, "alleviating a disease or disorder symptom," means reducing the severity of the symptom or the frequency with which such a symptom is experienced by a subject, or both.

As used herein, an "analog", or "analogue" of a chemical compound is a compound that, by way of example, resembles another in structure but is not necessarily an isomer (e.g., 5-fluorouracil is an analog of thymine).

An "antagonist" is a composition of matter which when administered to a mammal such as a human, inhibits a biological activity attributable to the level or presence of a compound or molecule of interest in the subject.

The term "antibody", as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

An "antibody heavy chain", as used herein, refers to the larger of the two types of polypeptide chains present in all antibody molecules.

An "antibody light chain", as used herein, refers to the smaller of the two types of polypeptide chains present in all antibody molecules.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antigenic determinant" as used herein refers to that portion of an antigen that makes contact with a particular antibody (i.e., an epitope). When a protein or fragment of a protein, or chemical moiety is used to immunize a host animal, numerous regions of the antigen may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "antimicrobial agents" as used herein refers to any naturally-occurring, synthetic, or semi-synthetic compound or composition or mixture thereof, which is safe for human or animal use as practiced in the methods of this invention, and is effective in killing or substantially inhibiting the growth of microbes. "Antimicrobial" as used herein, includes antibacterial, antifungal, and antiviral agents.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner", as used herein, refers to a molecule capable of binding to another molecule.

The term "biocompatible", as used herein, refers to a material that does not elicit a substantial detrimental response in the host.

As used herein, the term "biologically active" analog or derivative encompasses structural analogs and derivatives of the claimed compounds that have binding specificities and activities similar to the disclosed compounds.

The term "biological sample," as used herein, refers to samples obtained from a subject, including, but not limited to, sputum, CSF, blood, serum, plasma, gastric aspirates, throat swabs, skin, hair, tissue, blood, plasma, serum, cells, sweat and urine.

"Blood components" refers to main/important components such as red cells, white cells, platelets, and plasma and to other components that can be derived such as serum.

As used herein, the term "carrier molecule" refers to any molecule that is chemically conjugated to the antigen of interest that enables an immune response resulting in antibodies specific to the native antigen.

As used herein, the term "chemically conjugated", or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "compound", as used herein, refers to any type of substance or agent that is commonly considered a drug, or a candidate for use as a drug, as well as combinations and mixtures of the above. When referring to a compound of the invention, and unless otherwise specified, the term "compound" is intended to encompass not only the specified molecular entity but also its pharmaceutically acceptable, pharmacologically active analogs, including, but not limited to, salts, polymorphs, esters, amides, prodrugs, adducts, conjugates, active metabolites, and the like, where such modifications to the molecular entity are appropriate.

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

The term "delivery vehicle" refers to any kind of device or material which can be used to deliver compounds in vivo or can be added to a composition comprising compounds administered to a plant or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of H by an alkyl, acyl, or amino group.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used in the specification and the appended claims, the terms "for example", "for instance," "such as", "including" and the like are meant to introduce examples that further clarify more general subject matter. Unless otherwise specified, these examples are provided only as an aid for understanding the invention, and are not meant to be limiting in any fashion.

The terms "formula" and "structure" are used interchangeably herein.

As used herein, a "functional" molecule is a molecule in a form in which it exhibits a property or activity by which it is characterized. A functional enzyme, for example, is one that exhibits the characteristic catalytic activity by which the enzyme is characterized.

As used herein, "homology" is used synonymously with "identity".

The term "inhibit", as used herein, refers to the ability of a vector, transgene, or compound of the invention to reduce or impede a described function. Preferably, inhibition is by at least 10%, more preferably by at least 25%, even more preferably by at least 50%, and most preferably, the function is inhibited by at least 75%. The terms "inhibit", "reduce", and "block" are used interchangeably herein.

The term "inhibit a complex", as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the invention by any number of routes and means including, but not limited to, parenteral, systemic, enteral, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means.

The term "injury" refers to any physical damage to the body caused by violence, accident, trauma, or fracture, etc., as well as damage by surgery.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound.

Alternatively, the instructional material may be shipped separately from the container with the intention that the instructional material and the compound be used cooperatively by the recipient.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "modulate", as used herein, refers to changing the level of an activity, function, or process. The term "modulate" encompasses both inhibiting and stimulating an activity, function, or process.

The term "otherwise identical sample", as used herein, refers to a sample similar to a first sample, that is, it is obtained in the same manner from the same subject from the same tissue or fluid, or it refers a similar sample obtained from a different subject. The term "otherwise identical sample from an unaffected subject" refers to a sample obtained from a subject not known to have the disease or disorder being examined. The sample may of course be a standard sample. By analogy, the term "otherwise identical" can also be used regarding regions or tissues in a subject or in an unaffected subject.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "per application" as used herein refers to administration of a compositions, drug, or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "physiologically acceptable" ester or salt means an ester or salt form of the active ingredient which is compatible with any other ingredients of the pharmaceutical composition, which is not deleterious to the subject to which the composition is to be administered.

"Plurality" means at least two.

The term "prevent", as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate.

A "prophylactic" treatment is a treatment administered to a subject who does not exhibit signs of a disease or exhibits only early signs of the disease for the purpose of decreasing the risk of developing pathology associated with the disease, or is done before a specific surgical procedure, etc.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., The Peptides, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell". A gene which is expressed in a recombinant host cell wherein the gene comprises a recombinant polynucleotide produces a "recombinant polypeptide".

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

A "sample", as used herein, refers preferably to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest. A sample can also be obtained from cell or tissue culture.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard", as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%.

The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

A "subject" of analysis, diagnosis, or treatment is an animal. Such animals include mammals, preferably a human.

As used herein, a "subject in need thereof" is a patient, animal, mammal, or human who will benefit from the method of this invention.

The term "symptom", as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

"Tissue" means (1) a group of similar cells united to perform a specific function; (2) a part of an organism consisting of an aggregate of cells having a similar structure and function; or (3) a grouping of cells that are similarly characterized by their structure and function, such as muscle or nerve tissue.

The term to "treat", as used herein, means reducing the frequency with which symptoms are experienced by a patient or subject or administering an agent or compound to reduce the frequency with which symptoms are experienced.

As used herein, the term "treating" can include prophylaxis of the specific disorder or condition, or alleviation of the symptoms associated with a specific disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term to "treat", as used herein, means reducing the frequency with which symptoms are experienced by a patient or subject or administering an agent or compound to reduce the frequency with which symptoms are experienced.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein, the term "optionally substituted" typically refers to from zero to four substituents, wherein the substituents are each independently selected. Each of the independently selected substituents may be the same or different than other substituents. For example, the substituents of an R group of a formula may be optionally substituted (e.g., from 1 to 4 times) with independently selected H, halogen, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain and amino acid.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. AOptionally substituted aryl @ includes aryl compounds having from zero to four substituents, and Asubstituted aryl@ includes aryl compounds having one or more substituents. The term ($C_5$-$C_8$ alkyl)aryl refers to any aryl group which is attached to the parent moiety via the alkyl group.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable."

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds of the present invention contain one or more asymmetric centers in the molecule. In accordance with the present invention a structure that does not designate the stereochemistry is to be understood as embracing all the various optical isomers, as well as racemic mixtures thereof.

The compounds of the present invention may exist in tautomeric forms and the invention includes both mixtures and separate individual tautomers. For example the following structure:

is understood to represent a mixture of the structures:

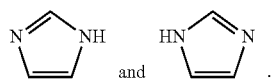

The term "pharmaceutically-acceptable salt" refers to salts which retain the biological effectiveness and properties of the compounds of the present invention and which are not biologically or otherwise undesirable. In many cases, the compounds of the present invention are capable of forming acid and/or base salts by virtue of the presence of amino and/or carboxyl groups or groups similar thereto.

Compounds of the present invention that have one or more asymmetric carbon atoms may exist as the optically pure enantiomers, or optically pure diastereomers, as well as mixtures of enantiomers, mixtures of diastereomers, and racemic mixtures of such stereoisomers. The present invention includes within its scope all such isomers and mixtures thereof.

Embodiments

As described herein, the compositions of the present invention comprise, as an active agent, compounds having the structure disclosed herein or any of the formulas disclosed herein in a pharmaceutically acceptable form. If desired, the compositions may further comprise one or more additional active agents. Where it is appropriate, any of the active agents may be administered in the form of the compound per se, and/or in the form of a salt, polymorph, ester, amide, prodrug, derivative, or the like, provided the salt, polymorph, ester, amide, prodrug or derivative is suitable pharmacologically. Where it is appropriate, salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically enriched form.

The values provided herein for radicals, substituents, and ranges, are for illustration only; they do not exclude other defined values or other values within defined ranges for the radicals and substituents. The disclosed compounds include compounds of the specific Formulas recited herein having any combination of the exemplary values, preferred values, and more preferred values described herein.

The compounds of the invention can be administered or used with other drugs and antimicrobial agents.

A composition of the invention may comprise additional ingredients. As used herein, "additional ingredients" include, but are not limited to, one or more of the following:

excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The pharmaceutical composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the condition or disease being treated, the sex and age of the subject, etc.

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes, or other agents may be used as adjunct therapies.

The values provided herein for radicals, substituents, and ranges are for illustration only; they do not exclude other defined values or other values within defined ranges for the radicals and substituents. The disclosed compounds include compounds of the specific Formulas recited herein having any combination of the exemplary values, preferred values, and more preferred values described herein.

Processes for preparing compounds of any of the formulas of the invention or for preparing intermediates useful for preparing compounds of any of the formulas of the invention are provided as further embodiments of the invention. Intermediates useful for preparing compounds of a formula of the invention are also provided as further embodiments of the invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Processes for preparing compounds of any of the formulas of the invention are provided as further embodiments of the invention and are illustrated by the following procedures in which the meanings of the generic radicals are as given above unless otherwise qualified.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of any of the formulas of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

It will be appreciated that compounds of the invention can be administered using various kinds of delivery systems and media. Furthermore, compounds of the invention can be administered in combination with other therapeutic agents and compounds and can be used with other kinds of treatments.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate, and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, in the range of 6 to 90 mg/kg/day, or in the range of 15 to 60 mg/kg/day.

The compound can be conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations.

Examples of antimicrobial agents that can be used as additional agents in a pharmaceutical composition of the present invention include, but are not limited to, isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, cikprofloxacin, doxycycline, ampicillin, amphotericine B, ketoconazole, fluconazole, pyrimethamine, sulfadiazine, clindamycin, lincomycin, pentamidine, atovaquone, paromomycin, diclarazaril, acyclovir, trifluorouridine, foscarnet, penicillin, gentamicin, ganciclovir, iatroconazole, miconazole, Zn-pyrithione, and silver salts, such as chloride, bromide, iodide, and periodate.

The method of the invention includes a kit comprising a compound identified in the invention and an instructional material which describes administering the compound or a composition comprising the compound to a cell or a subject to any target of interest, such as a surface. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure.

Therefore, the examples should be construed to encompass any and all variations which become evident as a result of the teaching provided herein.

Examples

Materials and Methods

SACLAC is a novel chlorine substitution analog of SABRAC. The synthesis of SABRAC is described in Camacho et al., 2013, J. Lipid Res., 54:1207-1220. Preparation of SABRAC (see Camacho et al.)—A solution of 1-hydroxybenzotriazole (18 mg, 0.13 mmol), the corresponding carboxylic acid (0.1 mmol), and N-(3-dimethylaminopropyl)-N'-ethylcarbodiimide hydrochloride (20 mg, 0.13 mmol) in $CH_2Cl_2$ (1 ml) was added to a mixture containing sphinganine (30 mg, 0.1 mmol), $NEt_3$ (30 µl, 0.2 mmol) in THF or $CH_3CN$ (1 ml). The resulting solution was stirred for 1 h at room temperature and concentrated at reduced pressure. The residue was taken up in $CH_2Cl_2$ (2 ml), washed with saturated aqueous $NaHCO_3$ solution (3×0.5 ml), and then the solvent was evaporated to give a crude mixture that was purified by flash chromatography on silica gel using a gradient of 0-5% $CH_2Cl_2$/MeOH to afford the pure amide in 70-85% yield.

Spectroscopic data— SABRAC: N-[(2S,3R)-1,3-dihydroxyoctadecan-2-yl]2-bromoacetamide. $^1$H-NMR (400 MHz, $CDCl_3$): 7.40 (1H, NH), 4.20 (2H), 4.05 (1H), 3.85 (1H), 3.83 (1H), 3.81 (1H), 1.55 (2H), 1.25-1.30 (26H), 0.88 (t, 3H). $^{13}$C-NMR (101 MHz, $CDCl_3$): 177.2, 74.2, 62.2, 54.0, 42.8, 34.7, 32.0, 29.8-29.6, 26.0, 22.8, 14.3.

SACLAC has the chemical name and structure:

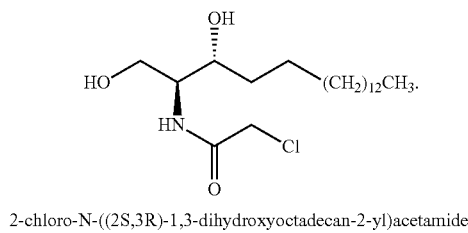

2-chloro-N-((2S,3R)-1,3-dihydroxyoctadecan-2-yl)acetamide

SACLAC also has the name (2S,3R)-2-chloro-N-(1,3-dihydroxyoctadecan-2-yl)acetamide. It was obtained by acylation of the corresponding sphingoid base with chloroacetyl chloride (1.2 equiv/mol) in $CH_2Cl_2/Et_3N$ at room temperature for 12 hours. Evaporation of the solvent afforded a crude, which was purified by flash chromatography on silica gel $CH_2Cl_2$/MeOH gradient (from 0-7%) to afford pure amides in 70-85% yield.

SACLAC-(2S,3R)-2-chloro-N-(1,3-dihydroxyoctadecan-2-yl)acetamide. HRMS calculated for $C_{20}H_{41}ClNO_3^+$ [M+1]: 378.2769, found 378.2764. $^1$H NMR (400 MHz, CDCl3, CD3OD? 9:1): δ 0.85 (t, 3H), 1.23 (broad, 28H), 1.51 (broad, 2H), 3.71 (dd, 1H, J=11.6, 3.4 Hz), 3.72 (m, 1H). 3.80 (m, 1H), 3.96 (dd, 1H, J=11.6, 3.4 Hz), 4.05 (s, 2H), 7.4 (d, 1H, J=8.4). $^{13}$C NMR (101 MHz, $CDCl_3$, $CD_3OD$? 9:1) δ 166.48, 73.27, 61.48, 54.08, 42.56, 34.25, 31.86, 29.6-29.3, 25.85, 22.62, 14.03.

NMR spectra were recorded at room temperature on a Varian Mercury 400 instrument. The chemical shifts (δ) are reported in ppm relative to the solvent signal, and coupling constants (J) are reported in Hertz (Hz). Deuterated solvents were used as internal standards (CDCl3: δ=7.26 ppm for 1H, δ=77.16 ppm for 13C; acetone-D6: δ=2.05 ppm for 1H, δ=29.84 ppm for 13C, CD3OD: δ=3.31 ppm for 1H, δ=49.00 ppm for 13C, and TFA (external standard) for 19F. Chemical shift (δ) values are reported in ppm. Signal characterization is described using the next abbreviations: s (singlet), d (doublet), t (triplet), q and m (multiplet). High Resolution Mass Spectrometry analyses were carried out on an Acquity UPLC system coupled to a LCT Premier orthogonal accelerated time-of-flight mass spectrometer (Waters) using electrospray ionization (ESI) technique.

Results

Known AC inhibitors have been screened and others made and tested, including the newly disclosed SACLAC, a ceramide analog, found herein to be an unexpectedly potent and selective inhibitor with clinical potential. Based on studies with similar inhibitors, SACLAC is expected to be a direct and irreversible AC inhibitor. This is a desirable quality for inhibitors, potentially minimizing off target effects and preventing the recovery of enzyme activity as drug concentrations decline following in vivo metabolism. SACLAC is a sphinganine derivative that irreversibly binds to its binding site and has an $IC_{50}$ of 46.7 nm. Other lysosphingolipids have also been made (Della Valle and Romeo, U.S. Pat. No. 5,519,007).

Figure 1B:
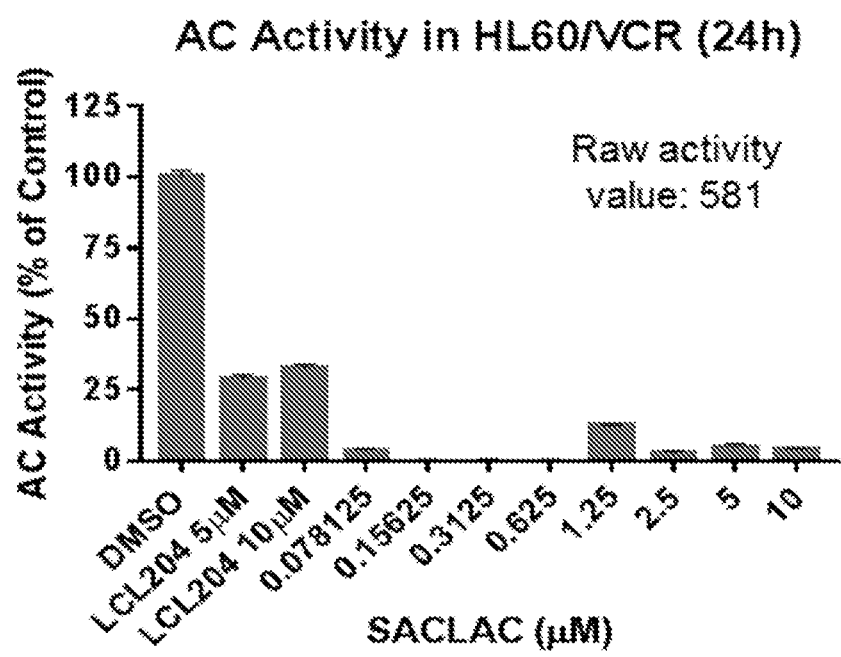
Figure 1C:
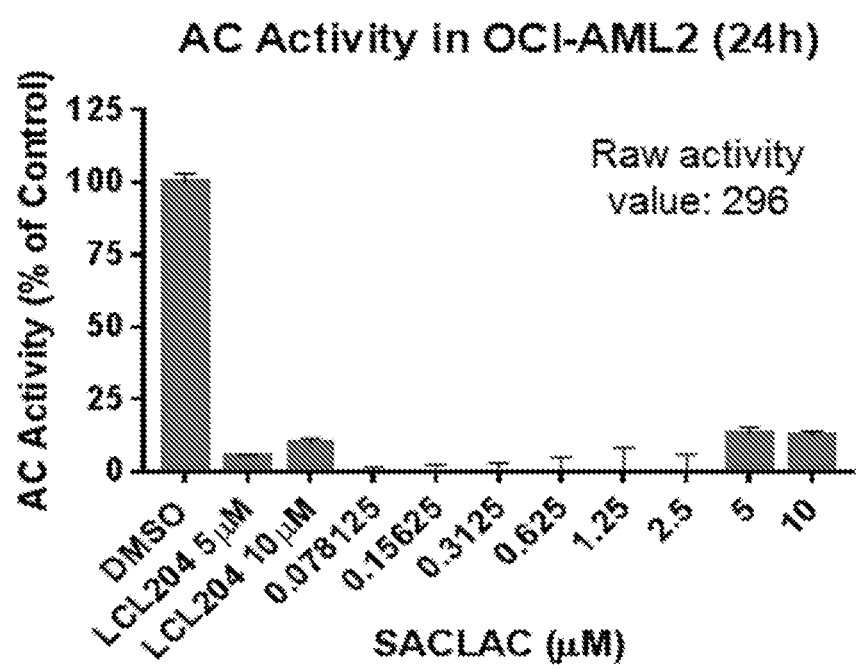
Figure 6:
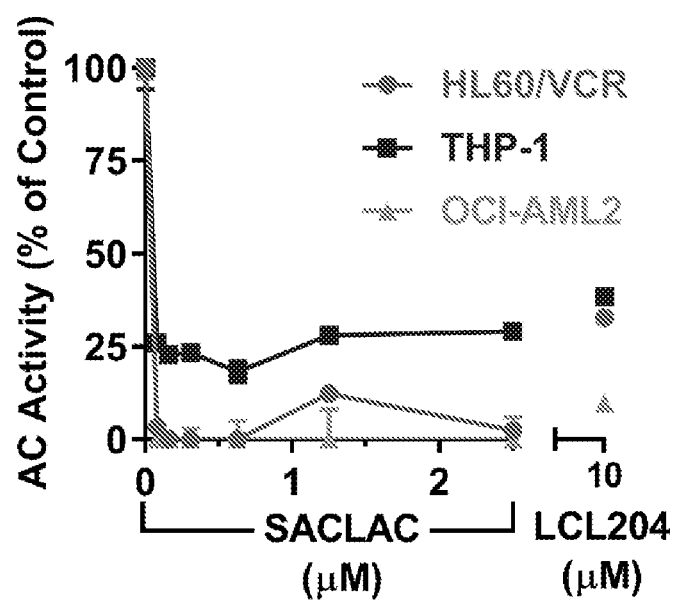
FIG. 6 depicts graphically that SACLAC treatment for 24 hours inhibited AC activity more potently than LCL204 in three human AML cell lines-(HL60/VCR, THP-1, and OCI-AML2 cells). The ordinate represents AC Activity as percent of control and the abscissa represents SACLAC or LCL204 concentration.

First, we demonstrated that SACLAC significantly reduced AC activity in AML cell lines (FIGS. 1A-C). AC activity was measured using previously published methods.[13,18,19] We compared the activity levels upon inhibition with SACLAC to previously published AC inhibitor LCL204, and show that SACLAC decreased AC activity at all tested doses in multiple AML cell lines. Furthermore, SACLAC inhibits AC in lysates from cells overexpressing the enzyme with an IC50 value of 46 nM. LC/MS analysis of tryptic digests of AC incubated with SACLAC showed the formation of the expected lipid modified peptide, the peptide comprising cysteine (C), threonine (T), serine (S), isoleucine (I), valine (V), alanine (A), glutamic acid (E), aspartic acid (D) and lysine (K). Notably, SACLAC mediated nearly complete inhibition at nanomolar concentrations in these two cell lines and unexpectedly exhibited far greater potency than LCL204. Further studies showed that SACLAC was effective at reducing AC activity in three different human AML cell lines (see FIG. 6). That is, SACLAC treatment (24 h) inhibited AC activity more potently than LCL204 in human three AML cell lines (HL60/VCR, THP-1, and OCI-AML2 cells).

Figure 2A:
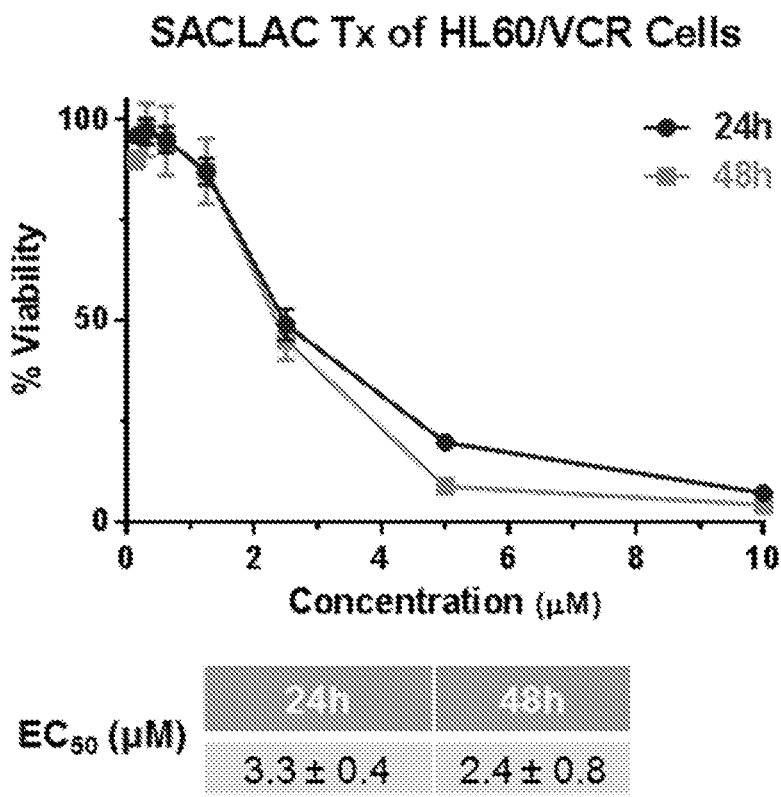
FIGS. 2A and 2B, shows that SACLAC treatment significantly reduces viability and induces apoptosis in AML cell lines. Representative human AML cell lines (FIG. 2A; upper and lower panels) HL60/VCR and (FIG. 2B; upper and lower panels) OCI-AML2 were treated with SACLAC for 24 and 48 hours. Viability was assessed by MTS assay at 24 and 48 hours and apoptosis was assessed by flow cytometry at 48 hours. Upper panels represent % viability and lower panels indicate % apoptosis.
Figure 2A:
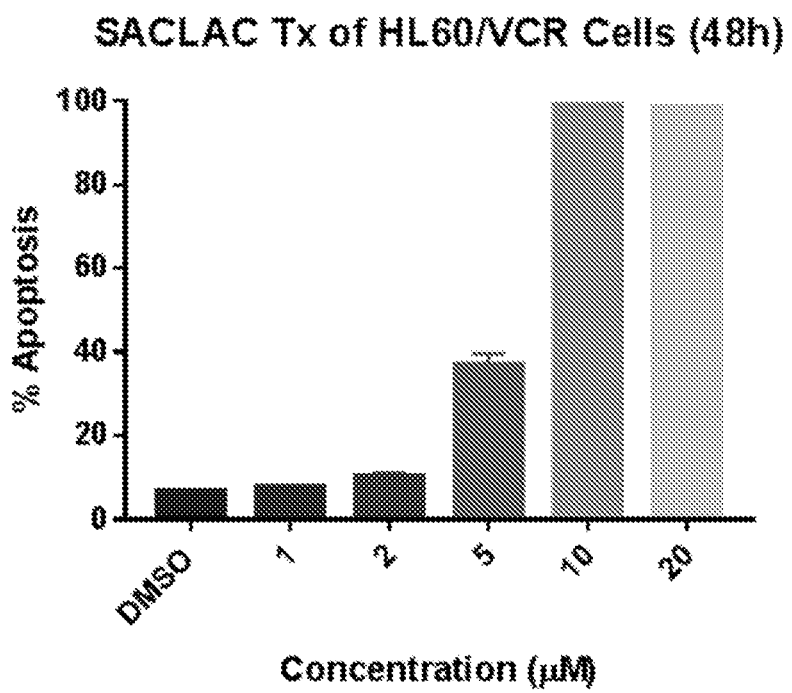
Figure 2B:
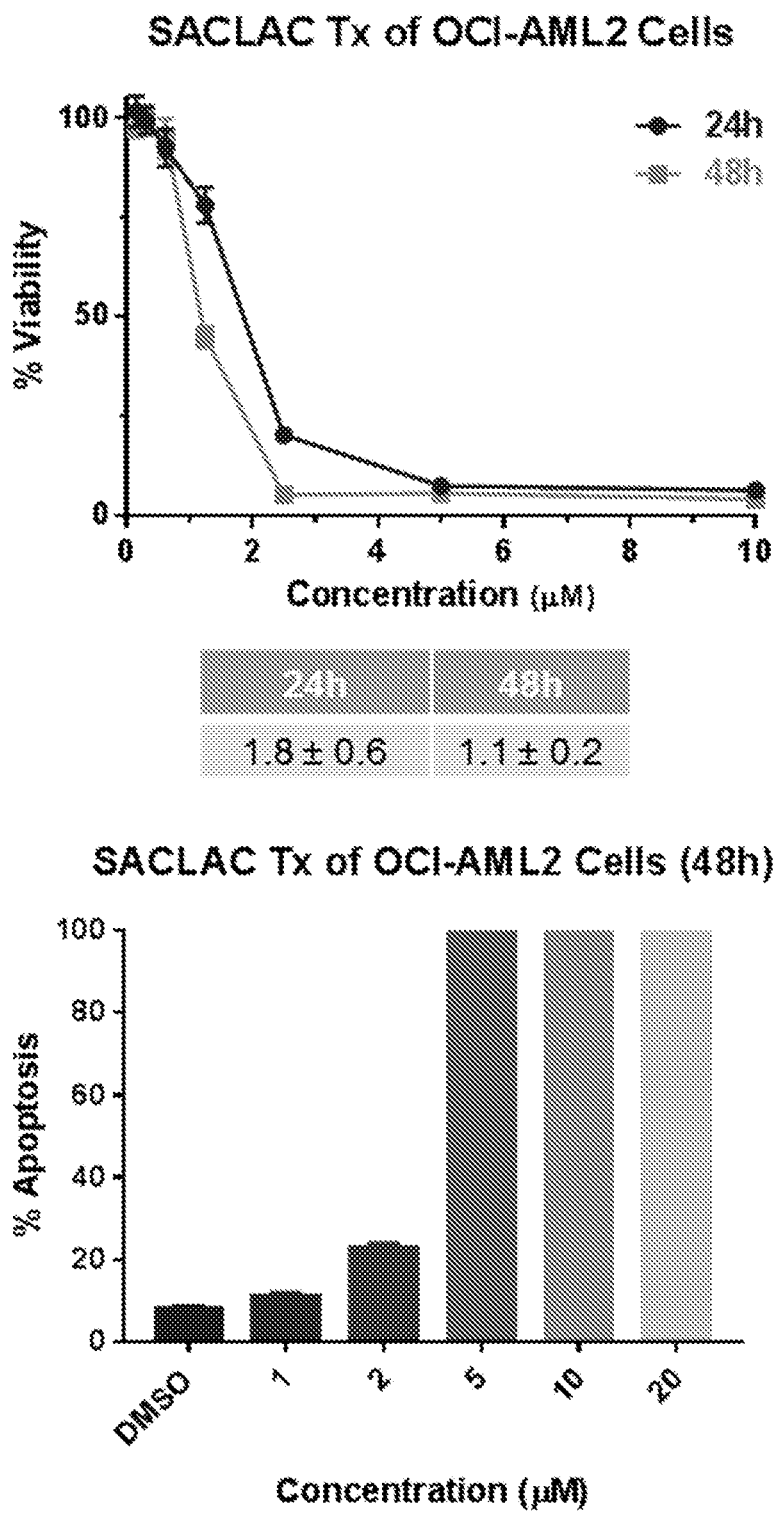

Next, we demonstrated that AC inhibitor SACLAC reduced viability and induced apoptosis in AML cell lines in a dose-dependent manner (FIGS. 2A-B). Two representative human-derived AML cell lines, HL60/VCR and OCI-AML2, are shown. These studies have been expanded to a large panel of additional human AML cell lines (n=30, Table 1). SACLAC exhibited efficacy in all cell lines tested including drug resistant variants HL60/ABTR, HL60/VCR, KG1A-R and KG1-R. $EC_{50}$ values for all AML cell lines were substantially lower than values that were derived from SACLAC treated normal controls at 24 h (13.5±7.1 M, see FIGS. 4A-4C and Table 2 below).

TABLE 1

SACLAC is widely potent in a panel of several AML cell lines.

| $EC_{50}(µM)$ | 24 h | 48 h |
| --- | --- | --- |
| NB4 | 0.2 | 0.6 |
| Kasumi-3 | 0.5 | 0.7 |
| MOLM-14 | 0.5 | 0.5 |
| OCI-AML3 | 0.6 | 0.4 |
| Kasumi-1 | 0.8 | 0.8 |

TABLE 1-continued

SACLAC is widely potent in a panel of several AML cell lines.

| $EC_{50}(\mu M)$ | 24 h | 48 h |
|---|---|---|
| SKNO1 | 0.9 | 0.8 |
| EOL-1 | 1.0 | 1.1 |
| U937 | 1.0 | 1.7 |
| MOLM-13 | 1.1 | 1.4 |
| NOMO1 | 1.1 | 0.8 |
| HEL | 1.2 | 1.6 |
| OCI-AML4 | 1.4 | 0.7 |
| SKM1 | 1.6 | 0.7 |
| ML2 | 1.7 | 1.8 |
| HL60 | 1.8 | 1.2 |
| OCI-AML2 | 1.8 | 1.1 |
| ME-1 | 2.1 | 1.2 |
| Kasumi-6 | 2.1 | 2.7 |
| MV4-11 | 2.3 | 1.3 |
| HL60/ABTR | 2.5 | 3.0 |
| THP-1 | 2.6 | 2.2 |
| SET2 | 2.6 | 3.3 |
| KGIa/ABTR | 2.9 | 2.7 |
| KGI | 3.2 | 2.7 |
| HL60/VCR | 3.3 | 2.4 |
| KGI/ABTR | 5.4 | 4.1 |
| KG1a | 5.6 | 3.5 |
| THF-1 | 6.7 | 4.8 |
| MM-6 | 7.8 | 6.0 |
| OCI-M2 | >10 | >10 |
| Average | 2.3 | 1.9 |

Human AML cell lines (n = 30) exhibit widespread sensitivity to SACLAC and SACLAC treatment reduced cell viability in all AML cells tested. OCI-M2 cells were 60% viable at the highest tested dose (10 µM).

SACLAC treatment reduced cell viability across a panel of 30 hAML cell lines (Table 1; mean EC50 2.3 µM) more so than normal PMBC and CD34+ controls (mean EC50 6.0 µM; n=10). Time course studies demonstrated apoptosis induction following SACLAC treatment with concurrent mitochondrial membrane depolarization. In summary, SACLAC exhibits significant improvement over LCL204 in all testing completed thus far and represents a promising option to advance an AC inhibitor to the clinic.

Figure 3A:
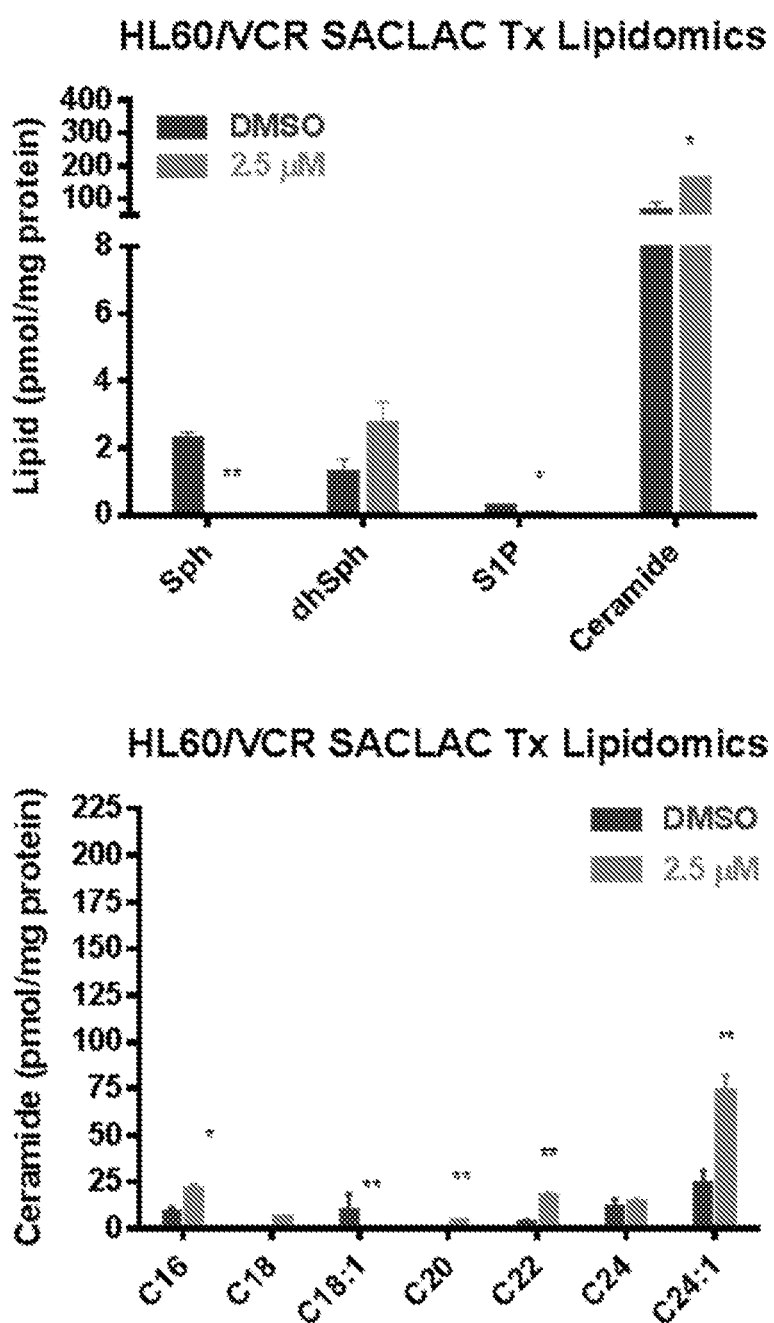
FIGS. 3A and 3B, shows that SACLAC treatment increases pro-death ceramides and decreases pro-survival S1P. Representative human AML cell lines (FIG. 3A; upper and lower panels) HL60/VCR and (FIG. 3B; upper and lower panels) OCI-AML2 were treated with SACLAC for 24 hours. Concentrations of lipid metabolites were determined by mass spectrometry. *, $p<0.05$; **, $p<0.01$ (Student's t-test). Upper panels represent Lipid in pmol/mg protein and lower panels represent Ceramide in pmol/mg protein.
Figure 3B:
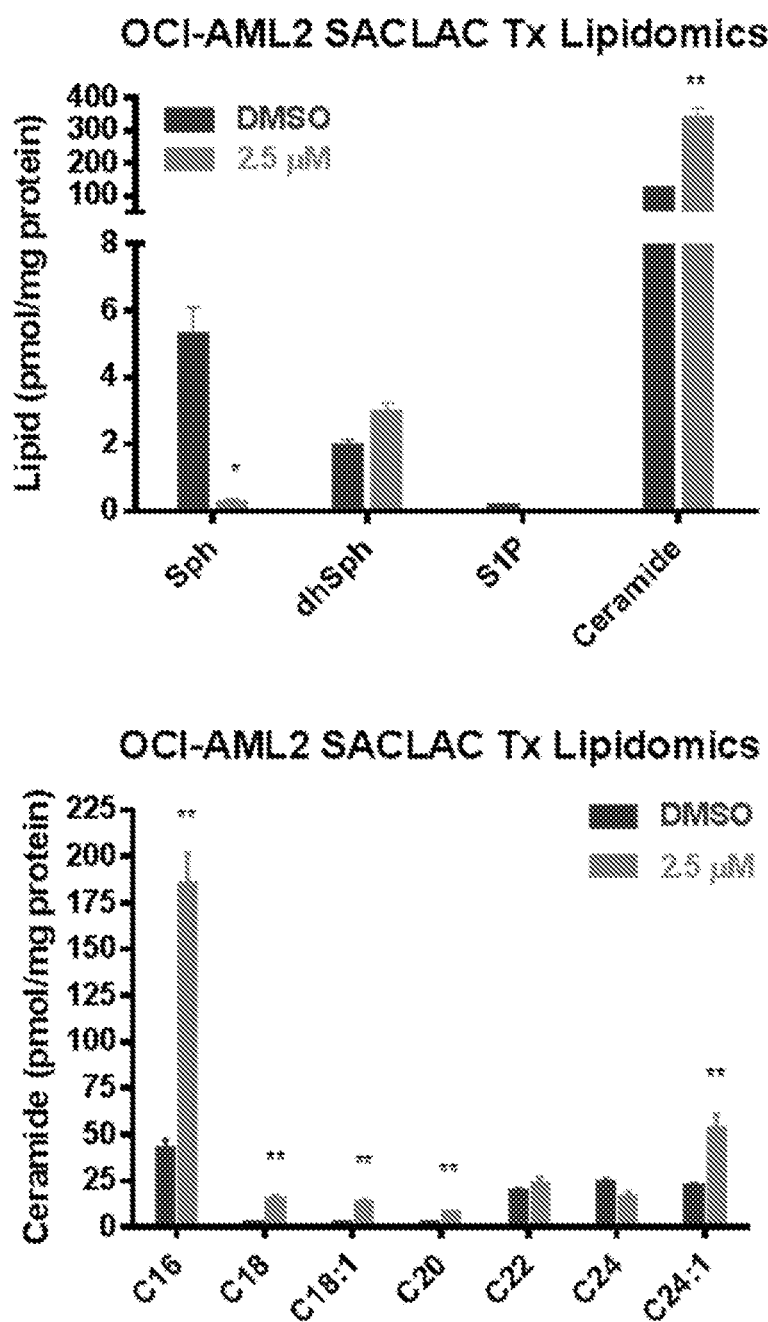

We also characterized lipid changes in response to SACLAC treatment in order to provide further evidence of potent AC inhibition (FIGS. 3A-3B). These experiments showed that SACLAC significantly reduced S1P pro-survival signals and increased ceramide pro-death signals, suggesting that SACLAC acts to rebalance the sphingolipid rheostat. Thus, the inhibitor blocks a common mechanism of ceramide detoxification in AML and is likely to provide therapeutic benefit by facilitating ceramide accumulation and apoptotic death of these proliferative cells.

Figure 4A:
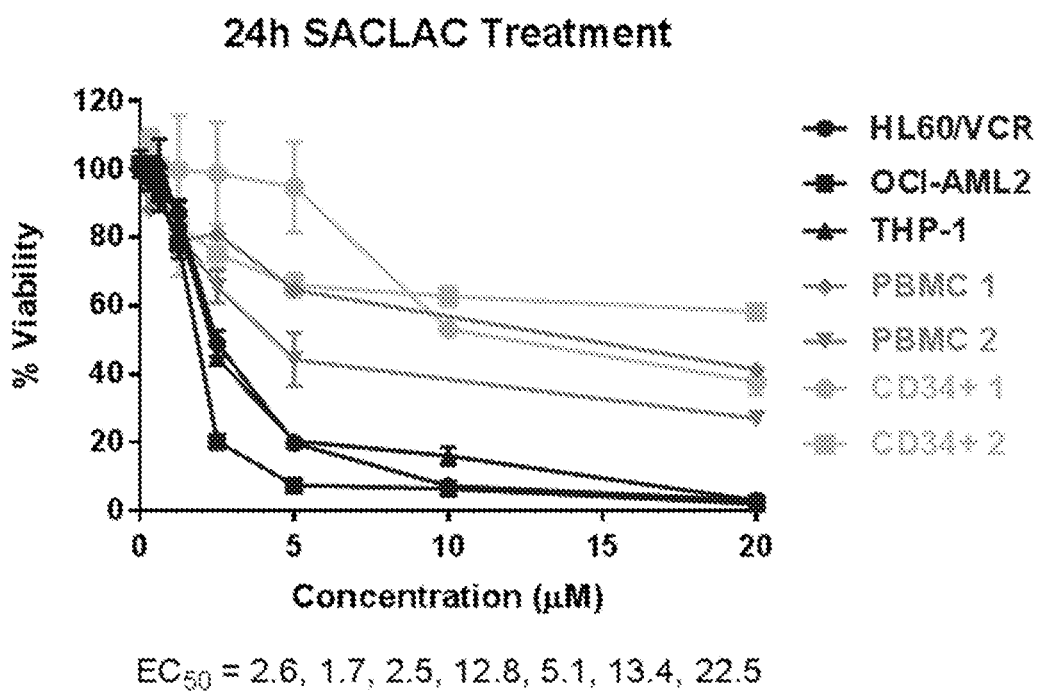
FIGS. 4A-C, shows that SACLAC is more selective for AML cell lines over normal cells. AML cell lines and normal samples (PBMCs and/or CD34+ cells) were treated for 24 hours with SACLAC (FIG. 4A-7 cell lines) and similar AC inhibitor SABRAC (2-bromo-N-((2S, 3R)-1,3-dihydroxyoctadecan-2-yl)acetamide) (FIG. 4B-four cell lines). Viability was assessed by MTS and Cell Titer Glo viability assays. $EC_{50}$ values (FIG. 4C) were graphed to visualize fold-change between AML and normal cells with treatment of each compound. $EC_{50}$ for SACLAC were 2.6, 1.7, 2.5, 12.8, 5.1, 13.4, and 22.5 µM and for SABRAC were 0.7, 0.02, 0.3, and 0.6 µM for FIGS. 4A and 4B respectively. Cells tested for SABRAC were HL60/VCR and OCI-AML2 AML cell lines and two normal PBMC control samples (PBMC1 and PBMC2). The same four cell types were tested for SACLAC, as well as the AML cell line THP-1 and two normal CD34+ cell control samples (CD34+1 and CD34+2).
Figure 4B:
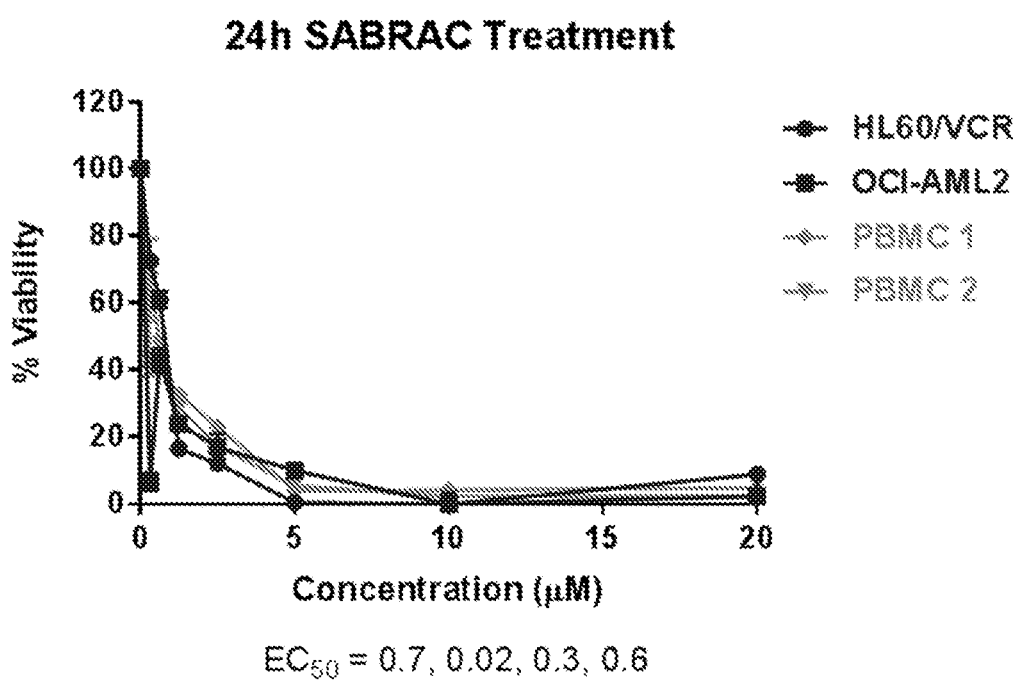
Figure 4C:
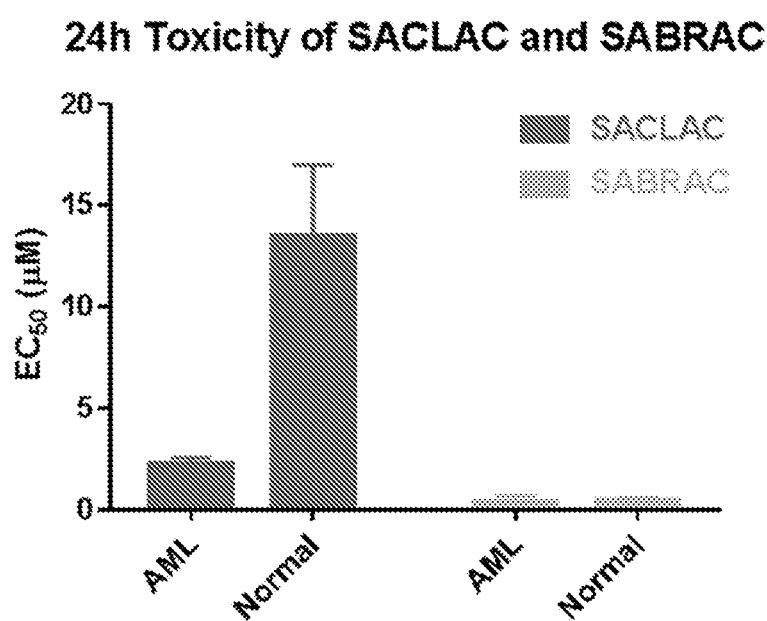

Next, we tested the toxicity of SACLAC and a similar published AC inhibitor SABRAC[17] to normal hematopoietic cells to ensure that AML cells are selectively targeted by the compound (FIG. 4A). Our studies show that SACLAC is nearly six times more potent against AML cells than normal cells, which suggests a substantial therapeutic window. This degree of selectivity was unexpected but extremely important for potential clinical use. This selectivity is a marked improvement from LCL204 treatment of AML and normal cells.[13] We also show that SACLAC is almost five times more selective for AML cells vs. normal cells than SABRAC (FIG. 4B-C, Table 2). Although SABRAC is structurally similar to SACLAC and was shown to be an efficient AC inhibitor for prostate cancer, we demonstrate that SACLAC is far more selective in our AML model than SABRAC. This remarkable increase in selectivity is a surprising discovery that greatly exceeds the predicted similarity in compound behavior that one may expect with a simple substitution of one halogen for another (Cl for Br). Therefore, SACLAC exhibits unique therapeutic potential for potent inhibition of AC and selective targeting of leukemic cells with minimal toxicity relative to published AC inhibitors such as LCL204[13] and SABRAC.[17]

TABLE 2

SACLAC is more selective for AML cell lines than SABRAC.

| $EC_{50}$ (µM) | Normal | AML | Fold Change | Selectivity of SACLAC/SABRAC |
|---|---|---|---|---|
| SACLAC | 13.45 | 2.27 | 5.93 | 4.75 |
| SABRAC | 0.45 | 0.36 | 1.25 | |

AML cell lines and normal samples (PBMCs and/or CD34+ cells) were treated for 24 hours with SACLAC and similar AC inhibitor SABRAC. $EC_{50}$ values were used to determine fold change of selectivity.

Figure 5A:
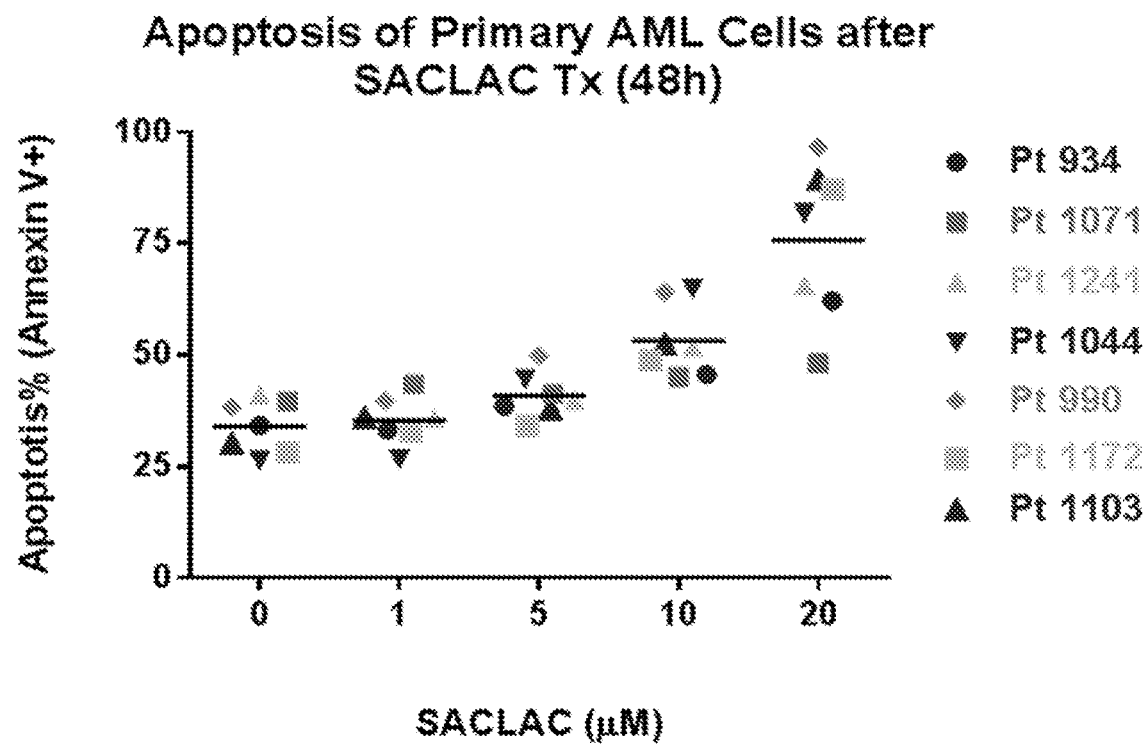
FIG. 5A demonstrates apoptosis—the ordinate represents Apoptosis % and the abscissa indicates SACLAC concentration (µM).
Figure 5B:
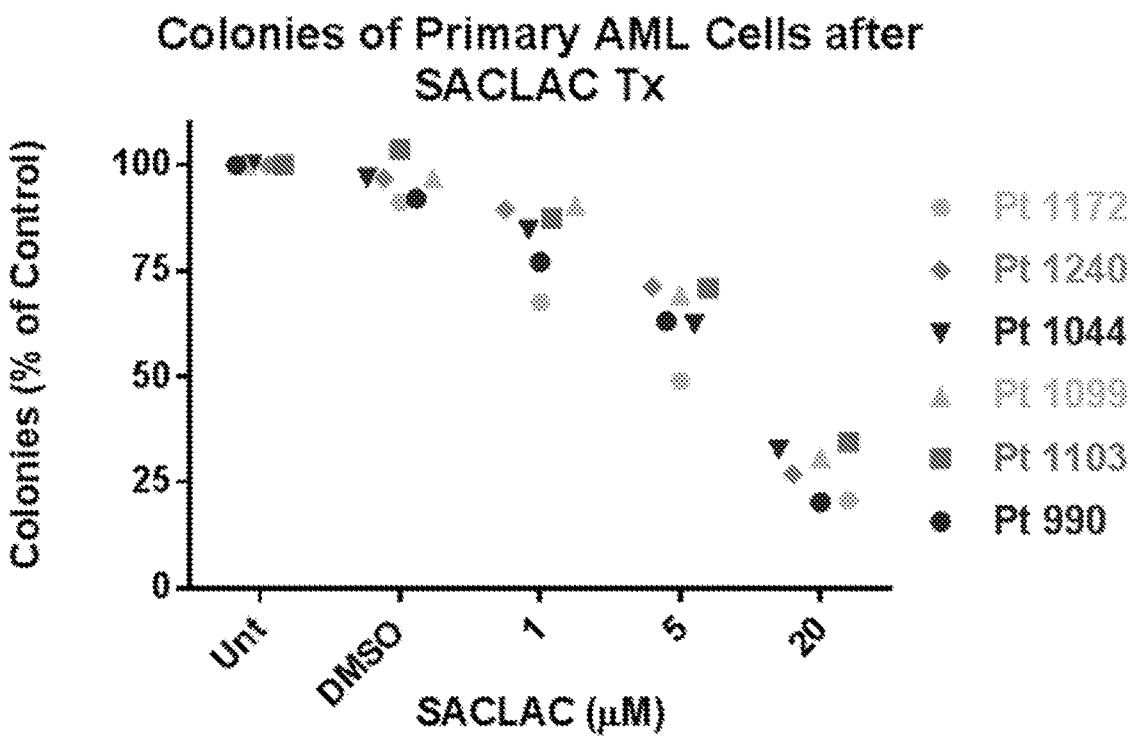
FIG. 5B demonstrates the effect of SACLAC on colony formation of primary AML cells from patients after SACLAC treatment. The ordinate represents Colonies (as % of control) and the abscissa represents the concentration of SACLAC (µM). Unt=untreated; DMSO=dimethyl sulfoxide vehicle control.

In addition, SACLAC effectively induced apoptosis and substantially reduced colony formation for a panel of primary AML patient samples, even under nutrient- and growth factor-rich culture conditions (FIGS. 5A-5B). These data demonstrate that SACLAC stands out from other AC inhibitors based on its potency, reduction of AC activity and selectivity for AML cells. Further, effects on patient samples strongly support the potential for clinical relevance of SACLAC. Overall, we demonstrate that SACLAC is a potent and selective AC inhibitor with several advantages over similar AC inhibitors. Based on the data presented here, we propose that use of SACLAC for treatment of AML is novel and clinically promising.

Preliminary results (not shown) indicate a maximum tolerated dose in vivo of at least about 50 mg/kg body weight. Pharmacokinetic studies are in progress to measure any accumulation of SACLAC in the blood following treatment. Initial studies are based on doses of 20 or 40 mg/kg body weight.

Figure 7:
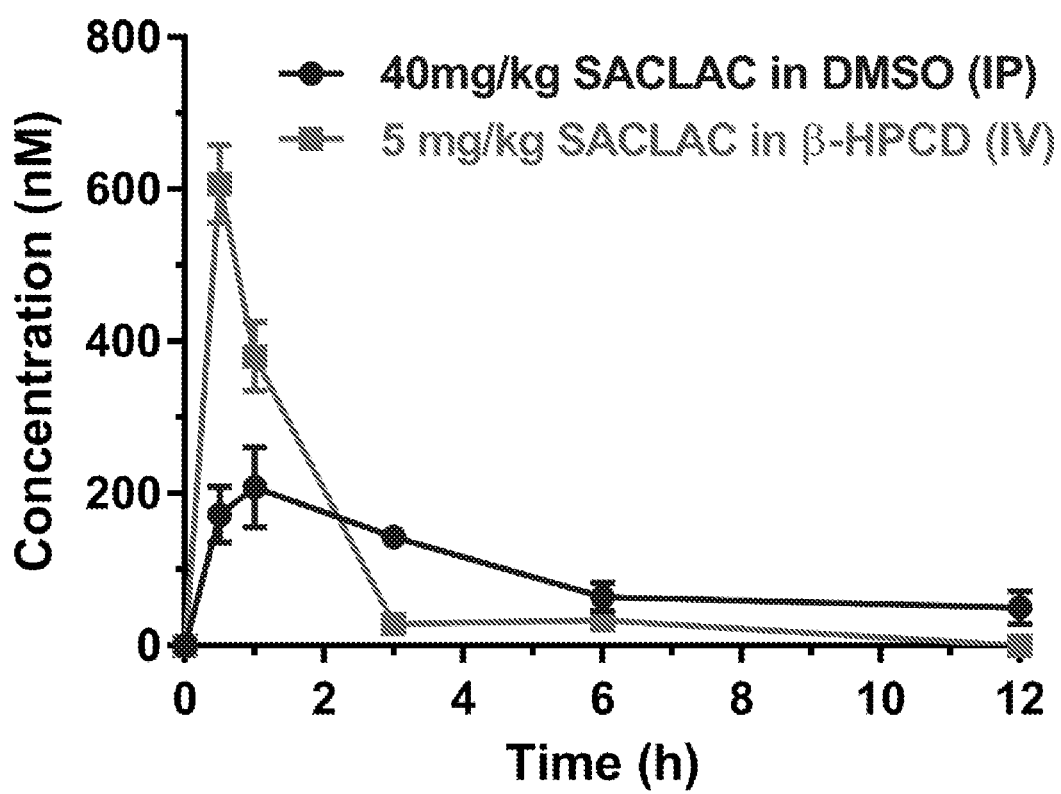
FIG. 7 graphically depicts SACLAC levels in mouse blood following administration intraperitoneally (i.p.) at 40 mg/kg body weight or intravenously (i.v.) at 5 mg/kg body weight. The ordinate represents Concentration (nM) and the abscissa Time (hours). DMSO (dimethyl sulfoxide) and β-HPCD (2-hydroxypropyl 3-cyclodextrin) represent the vehicle for SACLAC delivery.
Figure 8A:
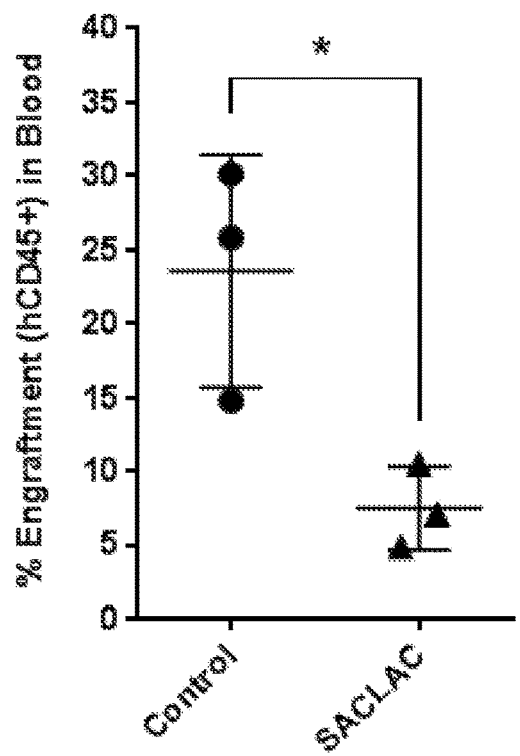
FIG. 8, comprising FIGS. 8A-C, demonstrates the effects of SACLAC in a human AML cell line mouse xenograft model. SACLAC treatment (5 mg/kg i.v. daily Monday to Friday for 18 days) reduced leukemic burden in MV4-11-engrafted NSG mice as indicated by (FIG. 8A) human CD45+ cells, (FIG. 8B) YFP expression and (FIG. 8C) percent double positive cells. * $p<0.05$.
Figure 8B:
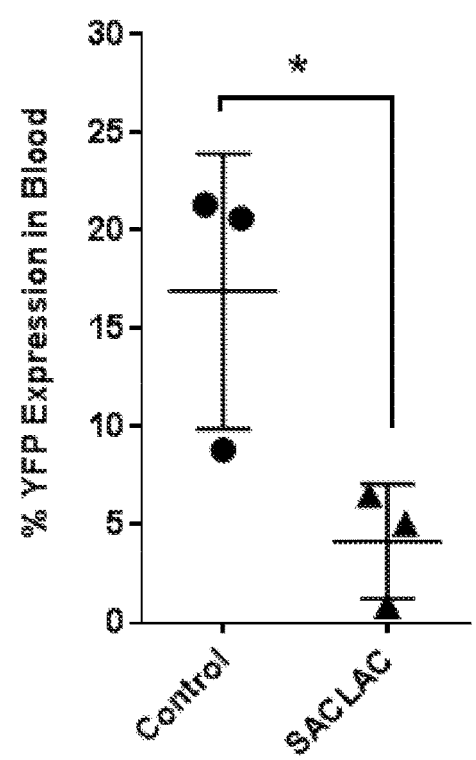
Figure 8C:
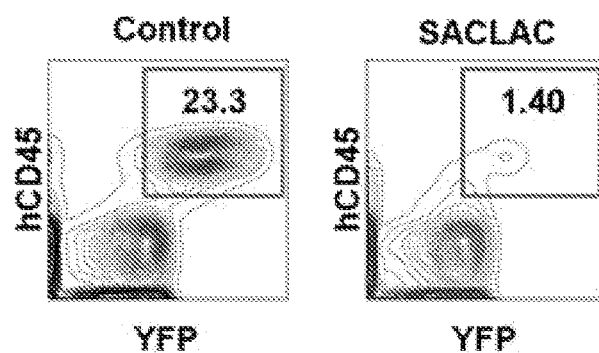

Serum concentrations of SACLAC were also determined following administration. (see FIG. 7). In spite of the promising results described above, it was known that SACLAC exhibits low solubility in vehicles for i.v. drug delivery and suboptimal uptake following i.p. injection. SACLAC was dissolved in dimethyl sulfoxide (DMSO) or 2-hydroxypropyl-β-cyclodextrin (β-HPCD). Serum levels were determined following injection of free SACLAC (i.p.—in DMSO at 40 mg/kg; or i.v.—5 mg/kg in β-HPCD). This study demonstrated low serum levels following i.p. delivery and great improvement with i.v. delivery. Efficacy was also demonstrated in a MV4-11 hAML xenograft model treated with SACLAC in β-HPCD (FIGS. 8A-8C). In the human AML xenograft model, SACLAC treatment (5 mg/kg i.v. daily M to F for 18 days) reduced leukemic burden in MV4-11-engrafted NSG (NOD.Cg-Prkdc$^{scid}$Il2rg$^{tm1/wjI}$/SzJ) mice as indicated by (8A) human CD45+ cells, (8B) YFP expression and (8C) percent double positive cells. * p<0.05. These studies demonstrate that drug delivery must be further enhanced in order to achieve additional reduction in leukemic burden and induce remission or cure. They also show our ability to generate and characterize in vitro functionality by modifying delivery and delivery systems, monitor PK and evolve our approaches based on experimental results in order to maximize in vivo efficacy.

DISCUSSION

There are five ceramidase genes that encode a family of enzymes whose optimal enzymatic activity is dependent upon pH: acid ceramidase (ASAH1, referred to as AC), neutral ceramidase (ASAH2) and three alkaline ceramidases (ACER1, 2, 3). AC is synthesized as an inactive precursor that is auto-cleaved to form the α and β subunits of the mature enzyme, which is localized in the lysosome. In multiple solid cancers, AC is upregulated and leads to proliferation whereas inhibiting AC results in ceramide accumulation and cell death. Studies disclosed herein also indicate that AC inhibition is broadly effective in AML due to its inherent dysregulation of sphingolipid metabolism.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

BIBLIOGRAPHY

1. Howlader, N. et al. SEER Cancer Statistics Review, 1975-2013. Available at: https://seer.cancer.gov/archive/csr/1975_2013/. (Accessed: 17th April 2017)
2. Klepin, H. D. & Balducci, L. Acute Myelogenous Leukemia in Older Adults. *The Oncologist* 14, 222-232 (2009).
3. Okuyama, N. et al. Prognosis of acute myeloid leukemia transformed from myelodysplastic syndromes: a multicenter retrospective study. *Leuk. Res.* 37, 862-867 (2013).
4. Leone, G., Voso, M. T., Sica, S., Morosetti, R. & Pagano, L. Therapy related leukemias: susceptibility, prevention and treatment. *Leuk. Lymphoma* 41, 255-276 (2001).
5. Papaemmanuil, E., Dohner, H. & Campbell, P. J. Genomic Classification in Acute Myeloid Leukemia. *N. Engl. J. Med.* 375, 900-901 (2016).
6. TCGA Network. Genomic and Epigenomic Landscapes of Adult De Novo Acute Myeloid Leukemia. *N. Engl. J. Med.* 368, 2059-2074 (2013).
7. Grimwade, D., Ivey, A. & Huntly, B. J. P. Molecular landscape of acute myeloid leukemia in younger adults and its clinical relevance. *Blood* 127, 29-41 (2016).
8. Metzeler, K. H. et al. Spectrum and prognostic relevance of driver gene mutations in acute myeloid leukemia. *Blood* 128, 686-698 (2016).
9. Hatzimichael, E., Georgiou, G., Benetatos, L. & Briasoulis, E. Gene mutations and molecularly targeted therapies in acute myeloid leukemia. *Am. J. Blood Res.* 3, 29-51 (2013).
10. Ryland, L. K., Fox, T. E., Liu, X., Loughran, T. P. & Kester, M. Dysregulation of sphingolipid metabolism in cancer. *Cancer Biol. Ther.* 11, 138-149 (2011).
11. Haimovitz-Friedman, A., Kolesnick, R. N. & Fuks, Z. Ceramide signaling in apoptosis. *Br. Med. Bull.* 53, 539-553 (1997).
12. Spiegel, S., Foster, D. & Kolesnick, R. Signal transduction through lipid second messengers. *Curr. Opin. Cell Biol.* 8, 159-167 (1996).
13. Tan, S.-F. et al. Acid ceramidase is upregulated in AML and represents a novel therapeutic target. *Oncotarget* 7, 83208-83222 (2016).
14. Evangelisti, C. et al. Therapeutic potential of targeting sphingosine kinases and sphingosine 1-phosphate in hematological malignancies. *Leukemia* 30, 2142-2151 (2016).
15. Alvarez, S. E. et al. Sphingosine-1-phosphate is a missing cofactor for the E3 ubiquitin ligase TRAF2. *Nature* 465, 1084-1088 (2010).
16. Newton, J., Lima, S., Maceyka, M. & Spiegel, S. Revisiting the sphingolipid rheostat: Evolving concepts in cancer therapy. *Exp. Cell Res.* 333, 195-200 (2015).
17. Camacho, L. et al. Acid ceramidase as a therapeutic target in metastatic prostate cancer. *J. Lipid Res.* 54, 1207-1220 (2013).
18. Bedia, C., Camacho, L., Abad, J. L., Fabrias, G. & Levade, T. A simple fluorogenic method for determination of acid ceramidase activity and diagnosis of Farber disease. *J. Lipid Res.* 51, 3542-3547 (2010).
19. Gouazé-Andersson, V. et al. Inhibition of acid ceramidase by a 2-substituted aminoethanol amide synergistically sensitizes prostate cancer cells to N-(4-hydroxyphenyl) retinamide. *The Prostate* 71, 1064-1073 (2011).
20. Della Valle and Romeo, U.S. Pat. No. 5,519,007.
21. Tan et al., 2017, Expert Opinion on Therapeutic Targets, 21:6583-590, The emergence of acid ceramidase as a therapeutic target for acute myeloid leukemia (published online, 4/24/17).

What is claimed is:

1. A method for treating acute myeloid leukemia (AML) comprising administering to a subject in need thereof a pharmaceutical composition comprising a pharmaceutically acceptable carrier and an effective amount of 2-chloro-N-((2S,3R)-1,3-dihydroxyoctadecan-2-yl)acetamide (SACLAC),

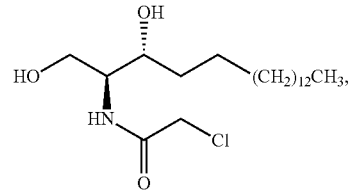

thereby treating said AML.

2. The method of claim 1, wherein said SACLAC is administered at a dose ranging from about 1 mg/kg body weight to about 100 mg/kg body weight.

3. The method of claim 2, wherein said SACLAC is administered at a dose ranging from about 2 mg/kg body weight to about 50 mg/kg body weight.

4. The method of claim 3, wherein said SACLAC is administered at a dose ranging from about 5 mg/kg body weight to about 40 mg/kg body weight.

5. The method of claim 2, wherein said SACLAC is administered at a dose selected from the group consisting of 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, and 40 mg/kg body weight.

6. The method of claim 1, wherein said pharmaceutical composition is administered once per day.

7. The method of claim 1, wherein said pharmaceutical composition is administered at least twice per day.

8. The method of claim 1, wherein said pharmaceutical composition is administered at least two times.

9. The method of claim 8, wherein a number of times said pharmaceutical composition is administered is selected from the group consisting of 100 or fewer times, 75 or fewer times, 50 or fewer times, 40 or fewer times, 30 or fewer times, 20 or fewer times, and 10 or fewer times.

10. The method of claim 1, wherein said method increases apoptosis in AML cells.

11. The method of claim 1, wherein said method reduces acid ceramidase activity in AML cells.

12. The method of claim 11, wherein said method increases pro-death ceramides and decreases pro-survival sphingosine-1-phosphate (S1P) in AML cells.

13. The method of claim 1, wherein said pharmaceutical composition is administered by a method selected from the group consisting of orally, intravenously, parenterally, and intraperitoneally.

14. A method for inducing apoptosis in an AML cell, said method comprising contacting said cell with an effective amount of SACLAC, thereby inducing apoptosis in said AML cell.

15. The method of claim 14, wherein said method reduces acid ceramidase activity in said AML cell.

16. The method of claim 14, wherein said method reduces S1P in AML cells and increases ceramide levels in AML cells.

17. A method for inhibiting growth of an AML cell, said method comprising contacting said cell with an effective amount of SACLAC, thereby inhibiting growth of said AML cell.

* * * * *